(12) United States Patent
Phillips et al.

(10) Patent No.: US 6,979,291 B1
(45) Date of Patent: Dec. 27, 2005

(54) SURGICAL RETRACTOR HAVING CURVED ARMS

(76) Inventors: Burns Phillips, 1838 Elm Hill Pike, Suite 119, Nashville, TN (US) 37210; Larry Griffith, 17637 Kettering Trail, Lakeville, MN (US) 55044

( * ) Notice: Subject to any disclaimer, the term of this patent is extended or adjusted under 35 U.S.C. 154(b) by 0 days.

(21) Appl. No.: 10/613,647

(22) Filed: Jul. 2, 2003

Related U.S. Application Data

(60) Provisional application No. 60/394,342, filed on Jul. 3, 2002.

(51) Int. Cl.[7] .............................. A61B 1/32

(52) U.S. Cl. .................................. 600/201

(58) Field of Search ................ 600/201, 203, 600/210, 213, 215, 216, 219, 221, 222, 224–229, 600/231–235; D24/135

(56) References Cited

U.S. PATENT DOCUMENTS

| | | | | | |
|---|---|---|---|---|---|
| 2,693,795 | A | * | 11/1954 | Grieshaber | 600/213 |
| 3,384,077 | A | * | 5/1968 | Gauthier | 600/234 |
| 3,747,592 | A | * | 7/1973 | Santos | 600/232 |
| 4,344,420 | A | * | 8/1982 | Forder | 600/232 |
| 4,989,587 | A | * | 2/1991 | Farley | 600/228 |
| 5,667,481 | A | * | 9/1997 | Villalta et al. | 600/224 |
| 6,017,306 | A | * | 1/2000 | Bigliani et al. | 600/234 |
| 6,371,911 | B1 | * | 4/2002 | Hossain et al. | 600/232 |
| 6,602,190 | B2 | * | 8/2003 | Dobrovolny | 600/234 |

\* cited by examiner

Primary Examiner—Eduardo C. Robert
Assistant Examiner—David Comstock
(74) Attorney, Agent, or Firm—Stephen J. Stark; Miller & Martin PLLC

(57) ABSTRACT

A surgical retractor having a lateral rack with two longitudinal arms extending therefrom. At least one of the arms has a curved segment. It is preferable that the curved segment extend at least one third the length of the arm and be concavely oriented toward the opposing arm.

13 Claims, 6 Drawing Sheets

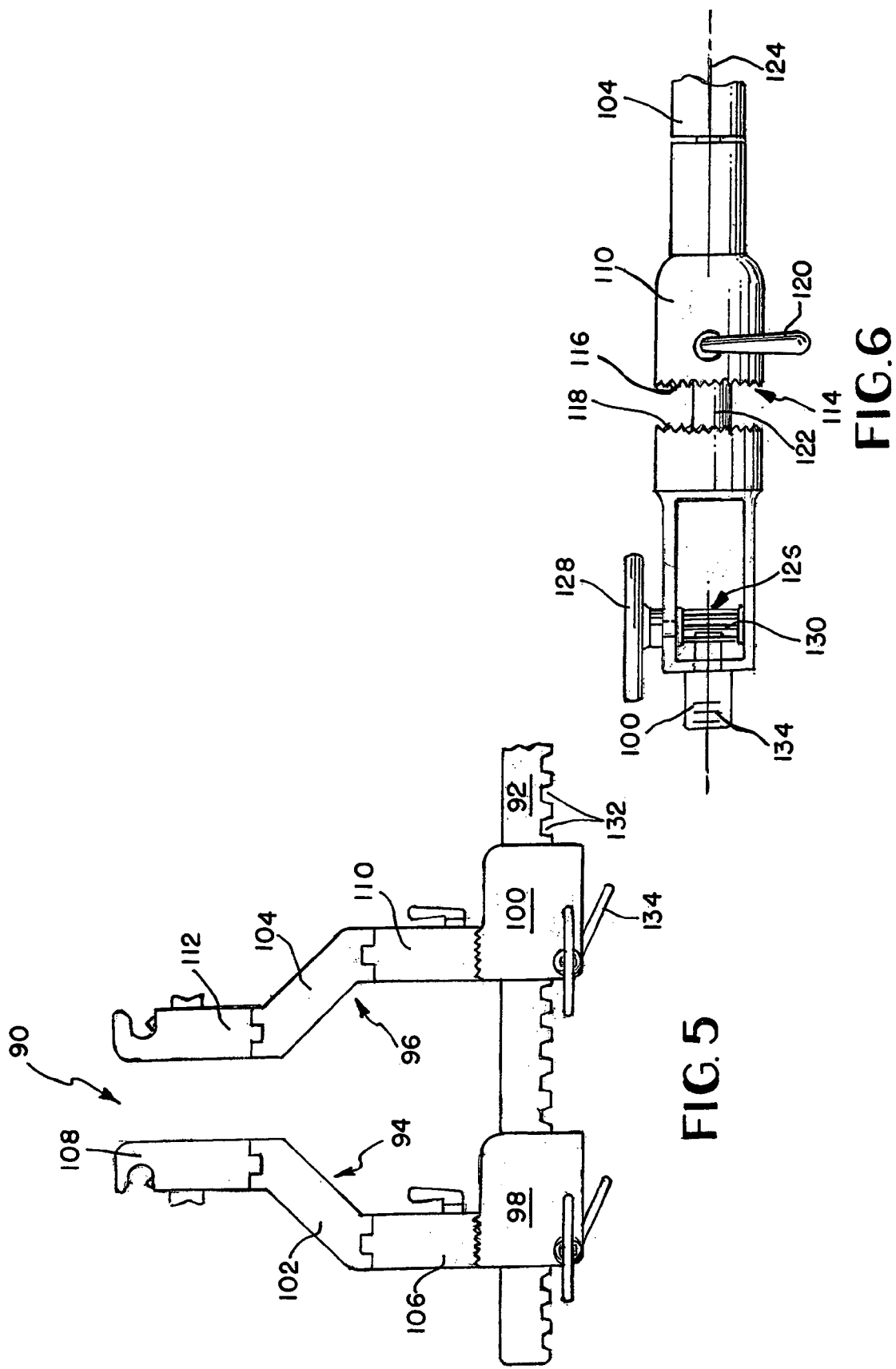

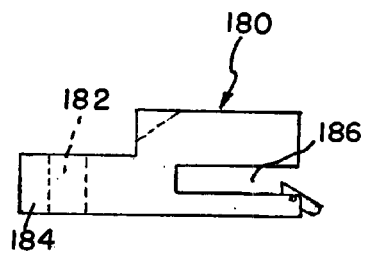
FIG.11
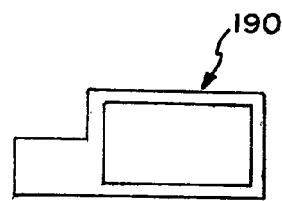
FIG.12
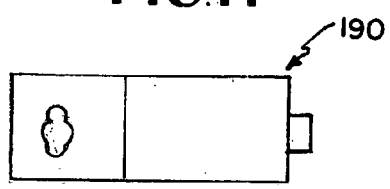
FIG.13
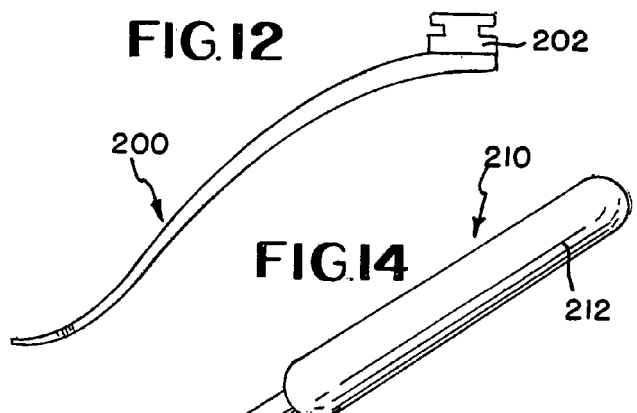
FIG.14
FIG.18
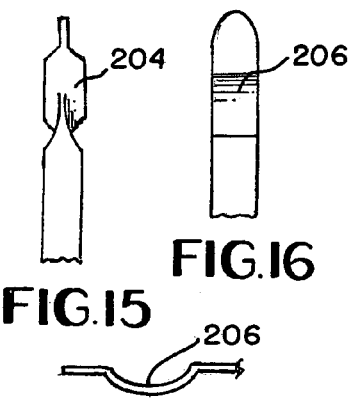
FIG.15
FIG.16
FIG.17
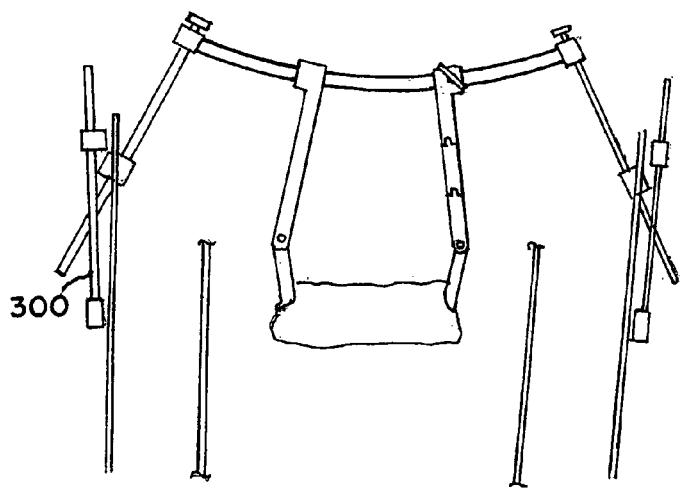
FIG.19

SURGICAL RETRACTOR HAVING CURVED ARMS

CLAIM OF PRIORITY

This application claims the benefit of U.S. Provisional Patent Application No. 60/394,342 filed Jul. 3, 2002.

BACKGROUND OF THE INVENTION

The method and devices disclosed are related to procedures and products utilized in minimally invasive joint surgery, and more particularly to retractors and associated components which are utilized in minimally invasive hip surgery.

BRIEF DESCRIPTION OF RELATED ART

Traditionally, hip surgery is an invasive procedure. Surgeons usually make large incisions and dislocate the femur at the hip. The femur is then placed across the patient's stomach while the surgeon accesses the hip area.

In order to shorten the recovery times, minimally invasive surgery has been proposed so that recovery times can be shortened which reduces the total costs of the procedure. In order to perform minimally invasive surgery on joints, such as the hip, new procedures and devices are necessary.

SUMMARY OF THE INVENTION

A need exists for a retractor support apparatus and associated components as well as a method for their use in minimally invasive joint surgery, including hip surgery.

A need also exists for the use of a retractor assembly and associated components for use in minimally invasive joint surgery.

Another need exists for an improved retractor.

Another need exists for an improved retractor clamp.

Yet another need exists for an improved retractor frame.

Accordingly a retractor assembly includes a retractor frame having two arms extending from a rack. The two arms may be curved, straight, or angled. The arms may also be hinged. At least one, and possibly both of the arms are locatable relative to the rack. Instead of being straight as has been traditionally done, the rack may be curved such as to define an arc of a circle, or having a changing radius such as a segment of a french curve.

Retractor clamps are utilized with the frame and may be connected to either the arms or the rack itself. Some retractor clamps are adapted to fit into position and need not necessarily have any other connecting mechanism to secure the clamp to the arm or rack. Other clamps have a retaining clip which may be spring biased to hold the clamp in a desired location on the arm or rack. Some clamps maintain a mount in a fixed position. Other clamps have mounts which are pivotable relative to their connection on the arm or rack. The rack or other portion of the system may then be connected to a bed rail or vertical post connected to the operating table or other fixture to fixedly secure the position of the retractor system components. The pivoting feature allows the mount to lift or push retractor blades into or out of an incision. The retractor clamps may be connected to a retractor handle and then to a blade. When the tissue is retracted to a desired position, the clamp is then secured to an arm or rack. The handle may then be disconnected from the blade.

Additionally, an extension arm is illustrated connected to an arm. The extension arm allows for substantially three hundred and sixty degrees of capability of positioning retractor clamps about an incision.

BRIEF DESCRIPTION OF THE DRAWINGS

The particular features and advantages of the invention as well as other objects will become apparent from the following description taken in connection with the accompanying drawings in which:

FIG. 3b is a back side plan view of the rack used in the retractor frame of FIG. 3a;

FIG. 4b is a side perspective view of the extension arm shown in FIG. 4a;

FIG. 5 is top plan view of a fourth alternatively preferred embodiment of the retractor frame of the present invention;

FIG. 6 is a side plan view of an arm of the fourth alternatively preferred embodiment in an unlocked position;

FIG. 11 is a side plan view of a first alternatively preferred retractor clamp of the present invention;

FIG. 12 is a side plan view of a second alternatively preferred retractor clamp of the present invention;

FIG. 13 is a top plan view of the retractor clamp of FIG. 12;

FIG. 14 is a side plan view of a retractor blade for use in the present invention;

FIG. 15 is a top plan view of the retractor blade end shown in FIG. 14.

FIG. 16 is top plan view of an alternatively preferred retractor blade end.

FIG. 17 is a side plan view of the retractor blade end of FIG. 16;

FIG. 18 is a side plan view of a handle for use with the retractor blades of FIGS. 15–17. and FIG. 19 is a perspective view of a surgical retractor system in use.

DETAILED DESCRIPTION OF THE DRAWINGS

Figure 1:
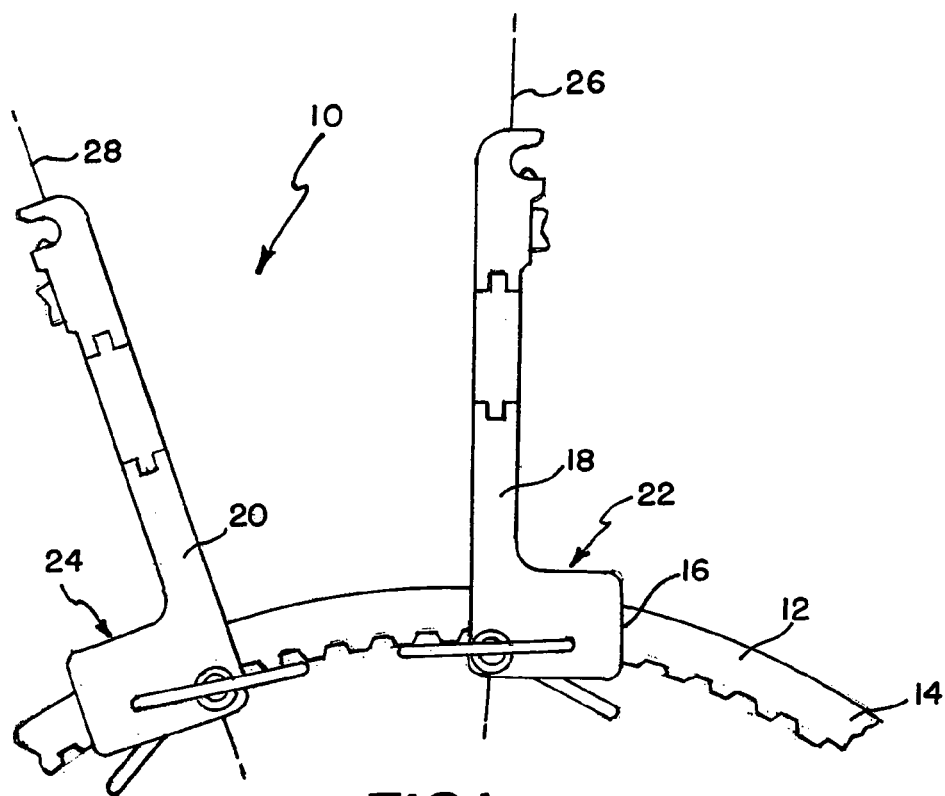
FIG. 1 is a top plan view of a retractor frame of a presently preferred embodiment of the present invention.

Accordingly, FIGS. 1–17 show a plurality of embodiments of the devices used with minimally invasive joint surgery. FIG. 1 shows a retractor frame 10 having a curved rack 12 or cross member. Racks of traditional frames are not believed to have been curved structures, however the curved rack 12 has been found helpful in applications such as joint surgery since the distal portion 14 of the rack 12 is further from the first arm 18 than the proximal portion 16. In a properly designed frame 10, the distal portion 14 will be out of the surgeon's way so that he or she can access the incision between the arms 18,20.

Another feature believed to be novel is the provision of two adjustment housings 22,24 which are slidably mounted relative to the rack 12 with each housing 22,24 respectively connected to the arms 18,20. This feature is believed to be helpful so that the rack 12 which is not intermediate the housings 22,24 may be positioned so that is opposite the surgeon, or otherwise located out of the way.

Figure 2:
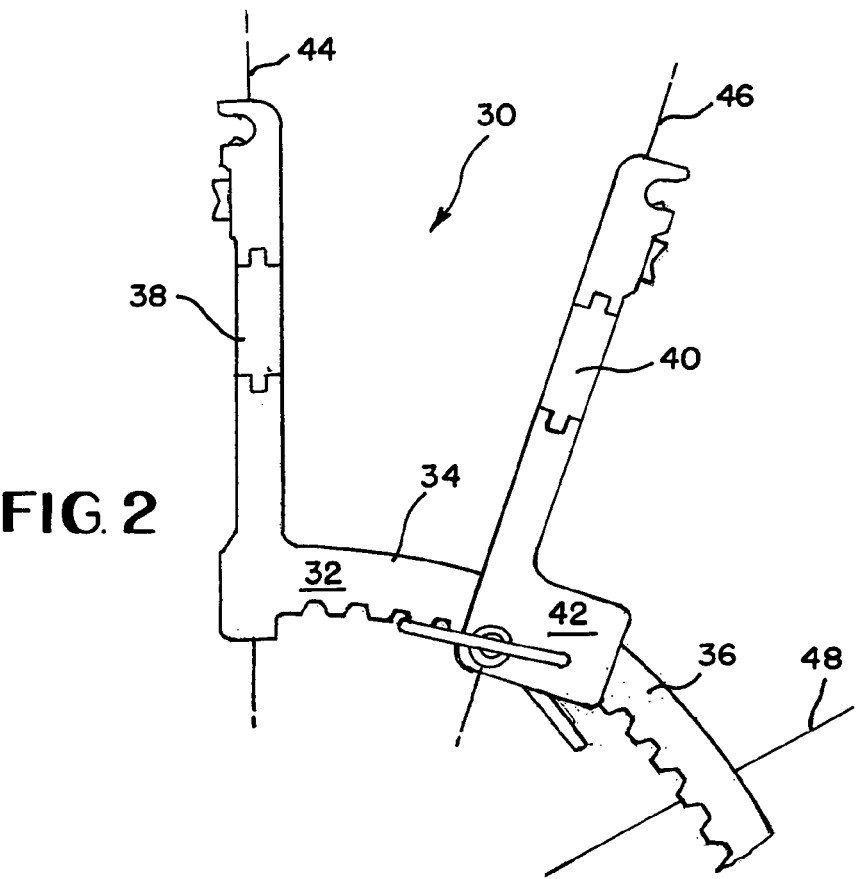
FIG. 2. is a top plan view of a first alternatively preferred embodiment of the retractor frame of the present invention.

In FIG. 2, frame 30 is illustrated with rack 32 having a first and second arcs 34,36 which would have two different radii. In other embodiments, the radii could be continuously changing such as provided by a french curve and/or include more distinct radii sections. This may assist in providing a desired angular relationship between the arms 38,40 for some surgical procedures at a desired spacing.

As can be seen by examining FIGS. 1 and 2, the arms 18,20 and 38,40 are not parallel. While the arms 18,20 and 38,40 could be parallel in some embodiments, such as shown in FIG. 4, the non-parallel nature of these arms is believed to be new to the art when straight arms are utilized. Additionally, as shown in FIG. 2, the angular relationship between the arms 38,40 can be varied based on where on the rack 32 the arms 38,40 are positioned, especially if each arm 38,40 has a housing 42 connected thereto to allow movement of the both arms 38,40 relative to the rack 32. As can be seen in FIG. 1, the angle between first and second axes 26,28 is about 15 degrees. Depending on the spacing between the housing for a fixed radius arc segment of rack 12, the angle will vary with the spacing.

In FIG. 2, since the rack has multiple radii arc segments, the angle between first and second axes 44,46 is not solely dependent upon spacing between the arms 38,40. While the three axes 44,46,48 are substantially equally spaced from one another where they intersect the rack 32, the angle between the first and second axes 44,46 is about 15 degrees while the angle between the second and third axes 46,48 is about forty five degrees. In other embodiments, the radii of arc segments may be different which of course would affect the angular relationship of the arms 38,40 as the spacing between the arms is increased or decreased.

Of course, housings may be designed or provided that allow for the arms 38,40 to be maintained parallel to the rack 32 through the changes in radii or for a specific radii by providing a connection of the arms at the housing allowing rotational movement of the arm relative to the housing or otherwise.

Figure 3A:
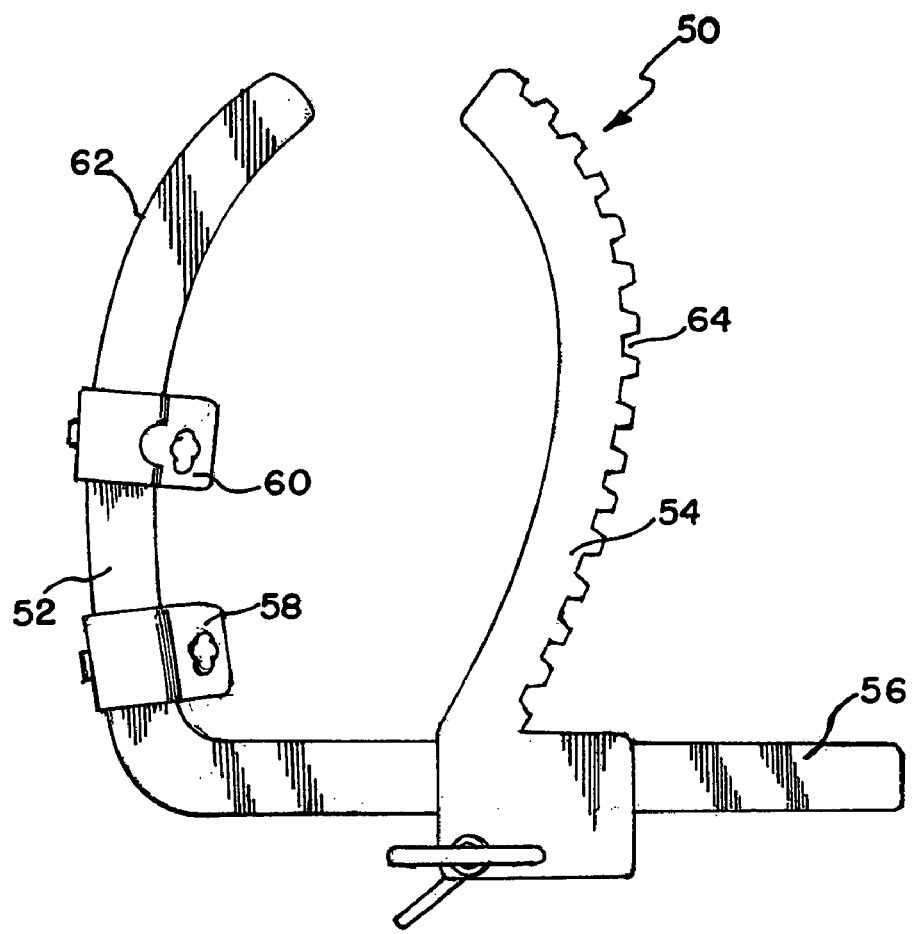
FIG. 3a is a top plan view of a second alternatively preferred embodiment of the retractor frame of the present invention with two retractor clamps connected thereto.
Figure 3B:
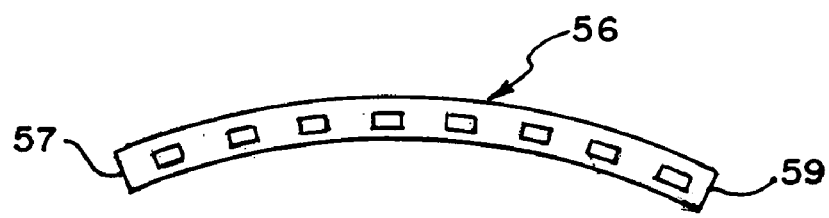

FIG. 3a shows an alternatively preferred embodiment of the preferred invention which shows some of the versatility of the retractor system described herein. Retractor 50 has a fixed arm 52 and a moveable arm 54. Unlike the hinged and straight arms shown in FIGS. 1 and 2, the arms 52,54 are curved along their length. This structure is believed to assist for certain shaped incisions. The rate of curvature may vary along the length, however the embodiment shown shows a relatively constant rate of curvature. The rack 56 may be substantially linear, or could be curved as shown in FIGS. 1, 2 and 3b. The arms 52,54 as well as the rack 56 may be provided with retractor clamps 58,60. Although the clamps are shown on the first arm 52, they may also be placed on the second arm 54 or the rack 56. The arms 52,54 may either have a smooth back 62, or a scalloped back 64 depending upon the needs of the user and the particular components to be utilized with the retractor frame 50. Of course, some racks 56 can be dome shaped or curved as shown in FIG. 3b as well as curved as shown in FIGS. 1 and 2 so that they are curved in more than two dimensions. The Adoming@ of the rack 56 has been found helpful in getting the ends 57,59 out of a surgeon=s way in some procedures.

Figure 4A:
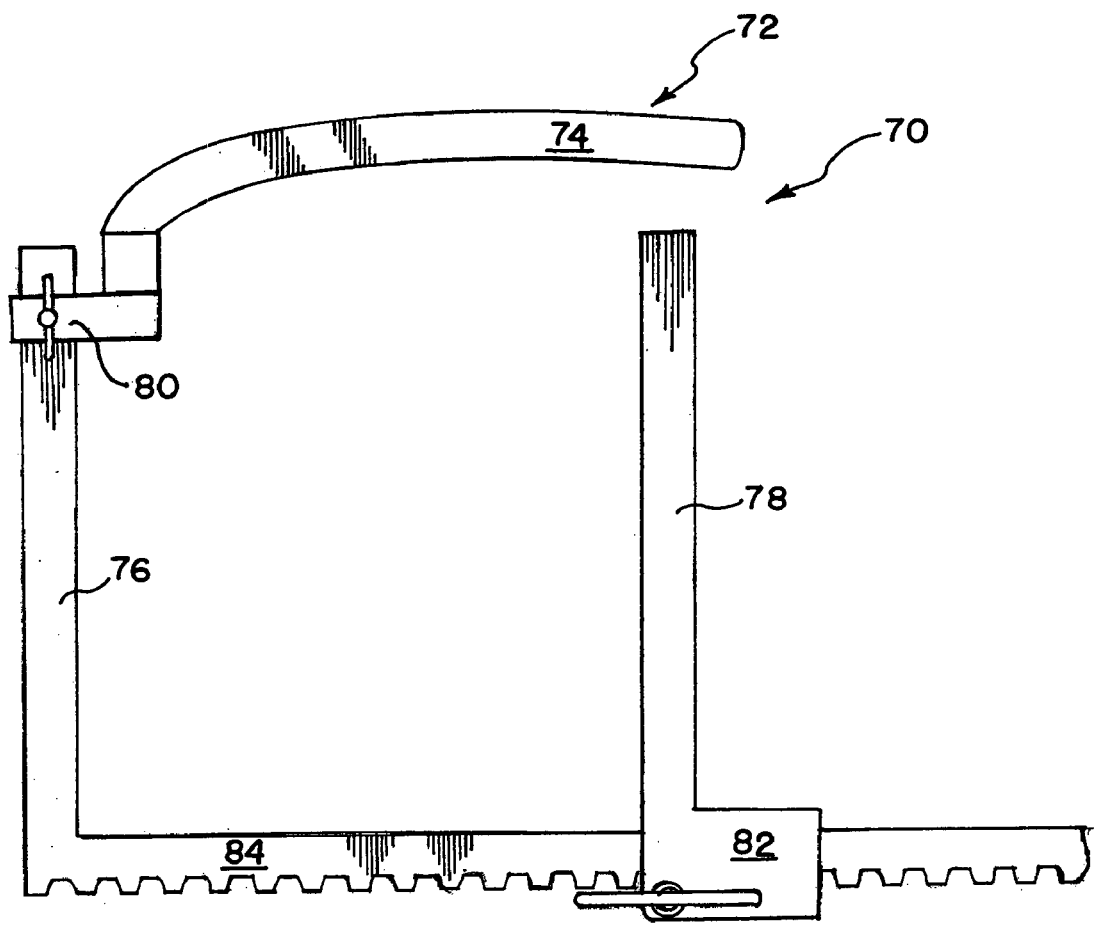
FIG. 4a is a top plan view of a third alternatively preferred embodiment of the retractor frame of the present invention with an extension arm connected thereto.
Figure 4B:
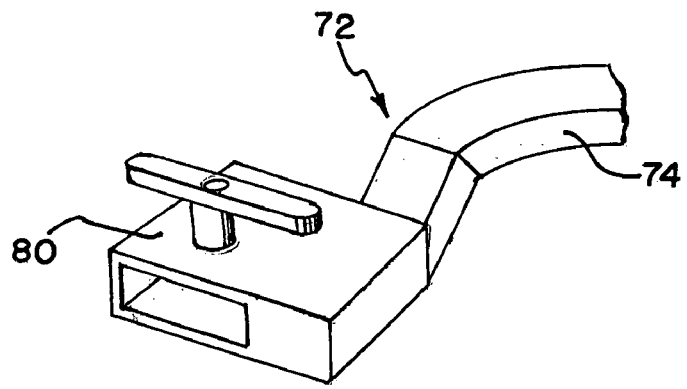

FIGS. 4a and 4b have been provided to illustrate a particular accessory for use with retractor frames, such as with a traditional frame 70 or any of the improved frames shown in FIGS. 1–3 or others. The extension arm 72 is believed to be a new development in the field of components utilized with retractor frames 70. The extension arm 72 may provide a surgeon the ability to provide substantially 360 degree coverage about an incision for locations to place a retractor clamp, and thus direct a retractor into an incision. This flexibility provides the surgeon with numerous options to provide a retracted incision while minimizing any impediments to his vision or ability to work within the incision.

Depending on the needs of the surgeon, the extension arm 72 may be substantially planar with the arms or it may elevate a support surface 74 above the arm, illustrated as first arm 76. It is connected so that the support surface 74 may pass over, or under, the second arm, such as second arm 78. Of course the extension arm 72 may be connected to the second arm 78 instead of the first arm 76 as illustrated. Additionally, the extension arm 72 may be equipped with a housing 80 which may either secure the extension arm 72 to an arm 76,78 or it may be somewhat similarly constructed as the housing 82 on either the first or second arms 76,78 to allow the surgeon or assistant to retract tissue away from the rack 84. Additionally, the extension 74 is illustrated as having a curved and/or domed support surface 74, however it could be straight, angled or otherwise constructed such as in a manner illustrated for the racks and arms shown herein. The use of the extension arm 74 is believed to be a huge improvement over the technique shown in U.S. Pat. No. 5,795,291, incorporated by reference, which requires using two retractor frames. Furthermore, the system utilized may be secured to a fixed support such as a vertical post 300, a rail of an operating table or other appropriate location as shown in FIG. 19.

FIGS. 5 and 6 show other features which may be incorporated into retractor frame construction for minimally invasive joint surgery. Frame 90 is illustrated having a rack 92 with arms 94,96 connected thereto. Housings 98,100 allow either of the arms 94,96 to be moved relative to the rack 92. The arms 94,96 have intermediate segments 102, 104 which are angled relative to first and second end segments 106,108 and 110,112, respectively. The first and second end segments 106,110 and 108,112 are parallel to one another, respectively.

From FIG. 6, the geometry of the arms 94,96 can be seen as being substantially rectangular except where the first segment 110 connects with housing 100. Although other geometrical arrangements can be utilized, in the embodiment shown in FIGS. 5 and 6, the first segment 110 is substantially round at base 114. The base 114 has serrated surface 116 which cooperates with serrated surface 118 on housing 100. Locking lever 120 locks and unlocks the first segment 110 relative to the housing 100.

The first segment 110 is illustrated as being rotatable relative to the housing 100 so that retractors may be positioned down into a wound or elevated relative to the wound when the first segment is in an unlocked configuration as shown in FIG. 6. This feature is also believed to be useful with racks which are dome shaped as shown in FIG. 3b to provide a desired angle of the arms relative to the rack (for instance, the planes the arms are in may be made to be parallel to one another even though the rack is not linear in some embodiments). By locking the first segment 110, the serrated surfaces 116,118 are brought into contact with one another to fix the rotational position of the arm 110 relative to the housing 110. The lever 120 is operably connected to a cam (obscured from view) within the first segment 110 which cooperates with post 122 to move the first segment 110 relative to the housing 110. Of course, there are other ways known in the art wherein the first segment 110, or a portion of the first segment 110 may be rotatably positioned relative to axis 124 and then secured at a desired position.

The first arm 94 is illustrated as having a similar angular adjustment feature as the second arm 96 which has been described in detail above. While this embodiment has hinged arms defined by segments 106,102,108 and 110,104,112, the arms of FIGS. 1–4 could also be provided with this capability.

The interior workings of the housing 100 are also illustrated in FIG. 6. While other devices are known in the art, the housing 100 has a driver 126 actuated by a handle 128. The driver 126 illustrated is a wheel with spokes 130 adapted to fit within slots 132 shown in FIG. 5. Release lever 134 may allow the driver 126 to act as a ratchet to move in only one direction when in the normally biased position illustrated, or it may be depressed to disengage the driver 126 from the slots 132 to allow the arm 96 to be positioned at the will of the user of the rack 92.

Figure 7:
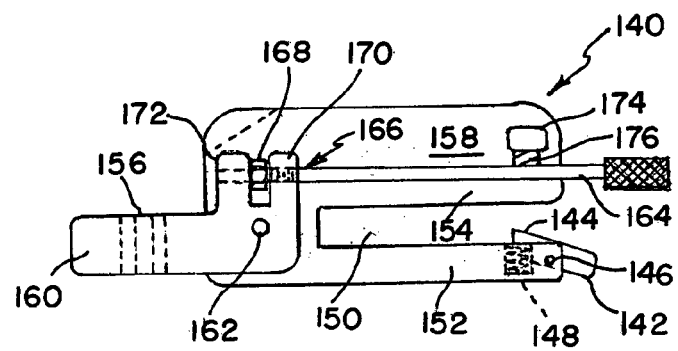
FIG. 7 is a side plan view of a preferred retractor clamp of the present invention.

Referring back to FIG. 3, two clamps 58,60, are illustrated. Details of these clamps and others are shown in FIGS. 7–13. FIG. 7 shows a side plan view of a clamp 140 which has a release button 142 for removing the clamp 140 once installed as shown in FIG. 3. The button acts on latch 144 about pivot 146. The latch 144 is normally biased by spring 148 into engagement with a back side 62 of an arm 52. While clamps have only been shown in FIG. 3, the same clamps could be utilized with any of the embodiments illustrated on any of the arms or racks.

The clamp 140 has a slot 150 which receives an arm or a rack therein. The latch 144 retains the inserted frame part. The slot 150 is illustrated as defined between upper and lower surfaces 152,154. The upper and lower surfaces 152,154 are illustrated as parallel to one another. The clamp has a mount 156 which connects to the member 158 containing the slot 150. The mount 156 of this embodiment is moveable relative to the member 158. This feature is not provided in the clamps shown in FIGS. 11–13.

Figure 8:
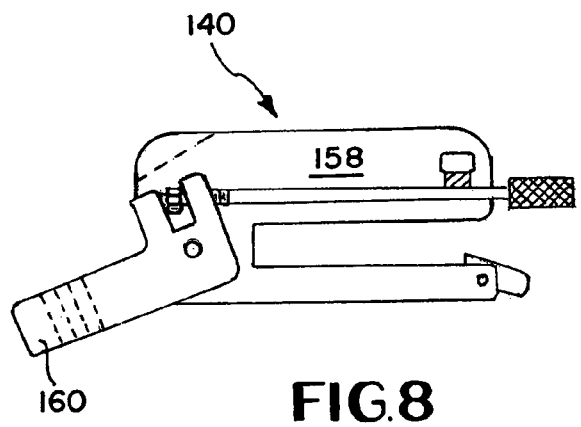
FIG. 8 is a side plan view of the retractor clamp of FIG. 7 with the mount pivoted downwardly.
Figure 9:
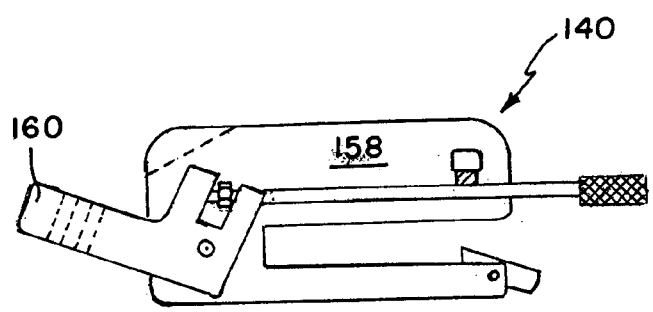
FIG. 9 is a side plan view of the retractor clamp of FIG. 7 with the mount pivoted upwardly.

In the clamp 140 of FIGS. 7–10, the mount 156 is connected to or more preferably a part of leg 160. Leg 160 is operably coupled to the member 158 by pivot 162. FIG. 7 shows the leg 160 substantially parallel to the slot 150. In order to change the angle of the leg 160 relative to the slot 150, operator 164 is utilized. By twisting on operator 164, threads at distal end 166 pass through nut 168 which is then moved along the axis of rotation of the operator 164. As the nut 168 moves, it acts against projections 170,172 to either pivot the leg downwardly as shown in FIG. 8, or upwardly as shown in FIG. 9. Of course, there are cutout portions in the projections 170,172 and leg 160 which receive the distal end 166 of the operator 164 to allow for this positioning.

Should a user desire to rapidly change the angle of the mount 156 relative to the slot 150, a quick release button 174 can be pushed which disengages threaded gear 176 to release the operator 164. Releasing the button 174 re-engages the gear 176 with the operator 164 to allow for continued adjustment with the operator 164.

Figure 10:
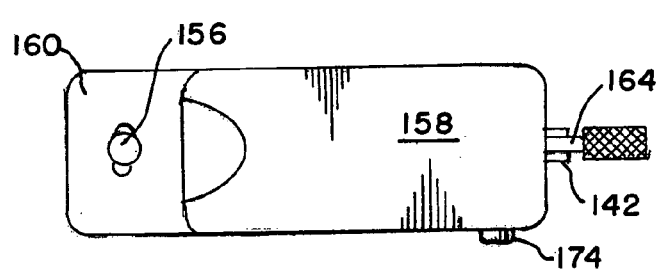
FIG. 10 is a top plan view of the retractor clamp of FIG. 7.

FIG. 10 shows a top plan view of the clamp 140. Groove 178 provides access to the mount from a hand held gripper which is illustrated in FIG. 18. When using a retractor blade equipped with a head as shown in FIG. 14, the head may extend up into the mount 156 where it is held by the hand held gripper and then the retractor is pulled or pushed into a desired location where the clamp may then be connected to an arm or rack and the hand held gripper may then release the clamp.

FIG. 11 shows an alternatively preferred embodiment of a clamp 180 which lacks the pivotal capability of the mount 182 and leg 184 relative to the slot 186. Apart from this difference, the clamps 140 and 180 are very similar. The top view of the clamp 180 will be very similar to that shown in FIG. 10 without the operator 164 extending as shown.

FIG. 12 shows another clamp 190 which slides onto an end of an arm or rack of a frame. The top view of the retractor clamp 190 of FIG. 12 is shown in FIG. 13. This clamp may either remain moveable along the arm or rack or may be outfitted with a connector such as shown on the extension arm in FIG. 4a or otherwise to secure the clamp 190 at a desired location relative to an arm or rack.

FIG. 14 shows a retractor blade 200 which has a head 202 and a contact surface 204. Although the contact surface 204 is illustrated as a "Hohmann" contact surface which is shown in detail in FIG. 15, FIGS. 16–17 show a "Hayes" contact surface 206. Of course other retractor blade contact surfaces which resemble paddles or other structures may also provide a contact surface for various uses. The head 202 may take on a number of shapes and is adapted to work with the selected mount of the clamp which will be utilized to retain the retractor blade.

FIG. 18 shows a hand held gripper 210. The gripper 210 has a handle 212 which twists relative to a shoe 214. As the handle 212 is twisted, a post 218 extends into a bore in the shoe 214 and onto a top of a head 202 of an inserted retractor blade 200 to secure the blade relative to the gripper 210. The head 202 has previously been inserted into slot 216 in the gripper 210. In order to release the head 202, the handle 212 is twisted in an opposite direction and the head 202 is released by the post 218. The head 202 may then be slid out of slot 216.

Numerous alternations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. The surgical retractor comprising:
   a rack having a proximal and distal portion,
   a first arm connected to a first location on the rack having an end spaced from the first location defining a length therebetween
   a second arm having a housing for slidably engaging a portion of the rack and an end spaced from the housing defining a length therebetween, said second arm selectively positionable on the rack intermediate the proximal and distal portions, said second arm having a continuously curved segment intermediate the housing and the end;
   said housing having an adjustment mechanism for allowing the positioning of the housing relative to the rack at a desired location and the at least temporary fixation of the housing at the desired location; and
   a retractor clamp selectively positionable along the curved segment at one of a plurality of locations; and wherein the continuously curved segment is concavely oriented toward the first arm.

2. The surgical retractor of claim 1 wherein the continuously curved segment of the second arm spans the length of the second arm.

3. The surgical retractor of claim 2 wherein the continuously curved segment has a constant rate of curvature.

4. The surgical retractor of claim 1 wherein the first and second arm are at least substantially coplanar.

5. The surgical retractor of claim 4 wherein the rack is substantially coplanar with the first and second arms.

6. The surgical retractor of claim 1 wherein the first arm further comprises a housing for slidably engaging a portion of the rack and an end spaced from the housing defining a length therebetween, said first arm selectively positionable on the rack intermediate the proximal end and distal end, said first arm having a continuously curved segment intermediate the housing and the end; and said housing having an adjustment mechanism for allowing the positioning of the housing relative to the rack at a desired location and the at least temporary fixation of the housing at the desired location on the rack.

7. The surgical retractor of claim 6 wherein the continuously curved segment of the first arms is concavely oriented relative to the second arm.

8. The surgical retractor of claim 1 wherein the continuously curved segment extends at least substantially the length of the second arm.

9. The surgical retractor of claim 1 wherein the continuously curved segment extends at least one third of the length of the second arm.

10. The surgical retractor of claim 9 wherein the continuously curved segment extends at least one half of the length of the second arm.

11. The surgical retractor of claim 1 wherein the first arm has a continuously curved segment intermediate the first location and the end, said continuously curved segment extending at least one third of the length of the first arm.

12. The surgical retractor of claim 11 wherein the continuously curved segment of the first arm extends at least one half the length of the first arm.

13. The surgical retractor of claim 12 wherein the continuously curved segment extends at least substantially the length of the first arm.

\* \* \* \* \*